United States Patent
Albers et al.

(10) Patent No.: US 6,455,059 B1
(45) Date of Patent: Sep. 24, 2002

(54) POLYETHER BLOCK AMIDES CONTAINING ACTIVE SUBSTANCES

(75) Inventors: Reinhard Albers, Leverkusen; Ralf Dujardin, Willich; Heinz Pudleiner, Krefeld; Joachim Simon, Düsseldorf; Joachim Wagner, Köln; Hartwin Hobler, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/831,227

(22) PCT Filed: Nov. 2, 1999

(86) PCT No.: PCT/EP99/08353

§ 371 (c)(1),
(2), (4) Date: May 7, 2001

(87) PCT Pub. No.: WO00/28814

PCT Pub. Date: May 25, 2000

(30) Foreign Application Priority Data

Nov. 12, 1998 (DE) .......................................... 198 52 190

(51) Int. Cl.⁷ ...................... A01N 25/00; A01N 25/08; A61K 9/14
(52) U.S. Cl. ...................... 424/405; 424/409; 424/484; 424/486
(58) Field of Search ................................ 424/405, 409, 424/484, 486

(56) References Cited

U.S. PATENT DOCUMENTS

| | | | |
|---|---|---|---|
| 5,019,096 A | 5/1991 | Fox, Jr. et al. | 623/1 |
| 5,165,952 A | 11/1992 | Solomon et al. | 427/2 |
| 5,556,383 A | 9/1996 | Wang et al. | 604/96 |
| 5,616,338 A | 4/1997 | Fox, Jr. et al. | 424/423 |

FOREIGN PATENT DOCUMENTS

| | | |
|---|---|---|
| DE | 4143239 | 7/1993 |
| FR | 2273021 | 12/1975 |
| WO | 96/22114 | 7/1996 |

OTHER PUBLICATIONS

Derwent Database, "Medical Material and its production" JP 08–280790, Iguci et al. (abstract).*

*Patent Abstract of Japan, vol. 1997, No. 02, Feb. 28, 1997, & JP 08 280790 A (Otsuka Pharmaceut Factory Inc.) Oct. 29, 1996, Zusammenfassung & Database WPI Week 9702, Derwent Publication Ltd., London, GB; An 1997–015196, XP002135906 & JP 08 280790A.

*Schierholz J.M. et al: "Controlled release of antibiotics from biomedical polyurethanes: Morphological and structural features", Biomaterials, GB, Elsevier Science Publishers BV., Barking, Bd. 18, Nr. 12, Jan. 1, 1997, Seiten 839–844, XP004064466.

* cited by examiner

Primary Examiner—Thurman K. Page
Assistant Examiner—Blessing Fubara
(74) Attorney, Agent, or Firm—Joseph C. Gil; Aron Preis; James R. Franks

(57) ABSTRACT

Molding compositions comprising polyether block amide and homogeneously distributed antimicrobially active substances are disclosed. The compositions are suitable for molding a variety of articles, notably medical articles.

11 Claims, No Drawings

POLYETHER BLOCK AMIDES CONTAINING ACTIVE SUBSTANCES

CROSS REFERENCE TO RELATED PATENT APPLICATIONS

The present patent application claims the right of priority under 35 U.S.C. §119 and 35 U.S.C. §365 of International Application No. PCT/EP99/08353, filed Nov. 2, 1999, which was published in German as International Patent Publication No. WO 00/28814 on May 25, 2000, which is entitled to the right of priority of German Patent Application No. 198 52 190.1, filed Nov. 12, 1998.

FIELD OF THE INVENTION

The invention relates to polyether block amides (PEBAs) which contain homogeneously distributed antimicrobial active substances, a process for their preparation and their use in medical articles.

BACKGROUND OF THE INVENTION

Vascular, catheter-associated infections are an important reason for the morbidity and mortality of patients in intensive care units. Recent studies have shown that up to 16% of patients fitted with a catheter in this group of patients suffer catheter-induced sepsis. About 2% of these patients exhibit severe clinical complications, in particular endotoxic shock or acute organ failure. In the future, a further increase in the incidence of catheter infections may be expected since catheters are increasingly being used in modem intensive therapy during invasive monitoring or treatment strategies such as, for example, continuous haemofiltration.

Many studies have shown that coagulase-negative Staphylococci, the transient bacterium Staphylococcus aureus and various species of Candida are the main sources of catheter-associated infections. These microorganisms, which are always present on the skin, penetrate the physiological skin barrier during application of the catheter and thus gain access to the subcutaneous region and ultimately the bloodstream. The adhesion of bacteria to the surface of plastics is regarded as an essential step during the pathogenesis of foreign body infections. After adhesion of skin bacteria to the polymer surface, there follows proliferation of the bacteria and colonisation of the polymer. This is accompanied by the production of a biofilm due to bacterial excretion of extracellular glycocalyx. The biofilm supports adhesion of the pathogen and protects it from the body's own immune defence system. In addition, the biofilm forms a barrier which cannot be penetrated by many antibiotics. After increased proliferation of the pathogenic bacteria on the polymer surface, septic bacteraemia may finally occur.

Removal of the infected catheter is required to treat these types of infections since chemical treatment with antibiotics would require physiologically unacceptable large doses.

The use of central venous catheters therefore involves not only a high risk of infection for patients, but also results in enormous therapeutic follow-up costs.

This problem can only be solved to a partial extent by prophylactic measures such as, for example, hygienic precautions or routine endoluminal application of antibiotics. A rational strategy for preventing polymer-associated infections comprises modifying the polymer material used. The objective of this modification must be the inhibition of bacterial adhesion and the proliferation of bacteria which have already adhered, in order to prevent causal foreign body infections. This can be achieved, for example, by incorporating a suitable antimicrobial active substance in the polymer matrix (e.g. antibiotics) assuming that the active substance incorporated can also diffuse out of the polymer matrix. In this case, release of the active substance can be extended over a long time so that bacterial adhesion and proliferation on the polymer is prevented for a correspondingly long time.

Methods for the preparation. of polymers provided with antimicrobial systems for medical use are already known. In the many processes which have been described, the active substance is added using the following techniques:

a) adsorption on the polymer surface (passively or via surfactants)
b) introduction in a polymer coating which is applied to the surface of a moulded item
c) incorporation within the bulk phase of the polymeric supporting material
d) covalent bonding to the polymer surface.

DE-A-41 43 239, for example, describes a process for introducing (impregnating) active substances into the outer layer of medical articles. Here, the implantable device made of a polymer material is steeped in a suitable solvent. The polymer matrix is then modified in such a way that a pharmaceutically active substance or combination of active substances can penetrate into the polymer material of the implant. After removing the solvent the active substance is included within the polymer matrix. Following contact with a physiological medium, the active substance contained within the implantable device is released again by diffusion. The release profile can be adjusted by the choice of solvent and by varying the experimental conditions.

Polymer materials for medical applications which have active substance-containing coatings are mentioned, for example, in EP-A 328 421. Processes for preparing the antimicrobial active coatings and methods for applying these to the surfaces of medical devices are described. The coatings consist of a polymer matrix, in particular polyurethanes, silicones or biodegradable polymers, and an antimicrobial active substance, preferably a synergistic combination of a silver salt and chlorhexidine or an antibiotic.

A common feature of all the processes mentioned is that providing the medical device with an antimicrobial active substance requires an additional working stage, that is either pre-treatment of the polymer material prior to processing or post-treatment of the moulded item produced. This causes additional costs and results in an increase in the production time. Another problem resulting from the processes is the use of organic solvents, which generally cannot be removed from the material without leaving some traces in the material.

SUMMARY OF THE INVENTION

The object of the invention was to provide new polymer materials which are suitable for the production of medical moulded items for short-term implants, in particular catheters, and effectively prevent surface colonisation by bacteria for a long period (2–4 weeks).

Polyether block amides which contain homogeneously distributed antimicrobial active substances, which release a concentration of antimicrobial active substance at the surface sufficient to suppress colonisation by bacteria for a long time, have now been found. Thus the invention provides polyether block amides which contain a homogeneously distributed antimicrobial active substance.

DETAILED DESCRIPTION OF THE INVENTION

In principal, all active substances which have a broad activity spectrum towards the pathogenic microorganisms involved in polymer-associated infections, in particular towards coagulase-negative Staphylococci, *Staphylococcus aureus* and the Candida species, may be considered suitable as antimicrobial active substances. According to the invention, the antimicrobial active substances may also be used as active substance combinations in the moulded items, provided their effects are not antagonistic.

The antimicrobial active substance used must exhibit adequate (chemical) stability in the polymer matrix. In addition, the microbiological activity of the active substance should not be impaired in the polymer matrix and under the process conditions for incorporation. The active substance must therefore be stable at the temperatures of 150 to 200° C. required for thermoplastic processing of the polymer material.

Incorporation of the pharmaceutically active substance should not impair either the biocompatibility of the polymer surface or other polymer-specific properties of the polymer material (elasticity, resistance to tearing, etc.).

Suitable antibiotic active substances are, for example:
  older quinolones such as e.g. nalidixic acid, pipemidic acid and cinoxacin,
  newer quinolones such as e.g. ciprofloxacin, norfloxacin, ofloxacin, pefloxacin, enoxacin, preferably ciprofloxacin,
  anminoglycosides such as e.g gentamicin, kanamycin, amikacin, sisomycin, tobramycin, netilmicin, preferably gentamicin and kanamycin,
  macrolides such as e.g erythromycin, clarithromycin and azithromycin,
  polypeptides such as e.g bacitracin, mupirocin, thyrothricin (a combination of gramicidin and tryrocidin),
  lincomycins such as e.g. lincomycin and clindamycin,
  antimycobacterial agents such as e.g. rifampicin or fusidic acid.

The antimicrobial active substance may also be an antiseptic or a disinfectant, as long as the substance used has sufficient activity against the infection-causing species.

In addition substances (pro-drugs) may be used which release an antimicrobial active substance under the effects of microbial activity.

The active substances are preferably incorporated in a concentration corresponding to their antimicrobial activity. Active substance concentrations in a range from 0.01 to 10.0 wt. % are particularly preferably used.

According to the invention, suitable polyether block amides are, for example, those which consist of polymer chains which are built up from repeating units corresponding to formula I.

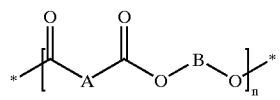
(I)

in which
  A is the polyamide chain derived from a polyamide with 2 terminal carboxyl groups by losing the latter and
  B is a polyoxyalkylene glycol chain derived from a polyoxyalkylene glycol with terminal OH groups by losing the latter and
  n is the number of units forming the polymer chain. The terminal groups are preferably OH groups or groupings from compounds which terminate polymerisation.

The dicarboxylic acid polyamides with terminal carboxyl groups are obtained in a known way, that is, for example, by polycondensing one or more lactams and/or one or more amino acids, also by polycondensing a dicarboxylic acid with a diamine, each in the presence of an excess of an organic dicarboxylic acid, preferably with terminal carboxyl groups. These carboxylic acids become constituents of the polyamide chain during polycondensation and are added on in particular at the ends of the chain, whereby an $\alpha,\omega$-dicarboxylic polyamide is obtained. Furthermore, the dicarboxylic acid acts as a chain-terminating agent, which is why it is used in excess.

The polyamide may be obtained from lactams and/or amino acids with a hydrocarbon chain containing 4–14 carbon atoms such as, for example, caprolactam, heptanolacatam, decanolactam, undecanolactam, dodecalactam, 11-amino-undecano or 12-amino-dodecano acid.

The condensation products of hexamethylene diamine with adipic, azelaic, sebacic and 1,12-dodecanedioic acid, and the condensation products of nonamethylene diamine and adipic acid may be mentioned as examples of polyamides which are produced by polycondensing a dicarboxylic acid with a diamine.

Dicarboxylic acids which are suitable for use during synthesis of the polyamide, that is, on the one hand, for fixing one carboxyl group at each end of the polyamide chain and, on the other hand, as a chain-terminating agent, are those with 4–20 carbon atoms, in particular alkanedioic acids such as succinic acid, adipic acid, suberic acid, azelaic acid, sebacic acid, undecanedioic or dodecanedioic acids, also cycloaliphatic or aromatic dicarboxylic acids such as terephthalic or isophthalic acids or cyclohexane-1,4-dicarboxylic acid.

The polyoxyalkylene glycols with terminal OH groups are unbranched or branched and contain an alkylene group with at least 2 carbon atoms. These are, in particular, polyoxyethylene, polyoxypropylene and polyoxytetramethylene glycol and copolymers thereof The average molecular weight of these OH-terminated polyoxyalkylene glycols may vary over a wide range; it is advantageously between 100 and 6000, in particular between 200 and 3000.

The proportion by weight of polyoxyalkylene glycol, with respect to the total weight of the polyoxyalkylene glycol and dicarboxylic acid polyamide used to prepare the PEBA polymer, is 5–85% preferably 10–50% .

Processes for synthesising these types of PEBA polymers are disclosed in FR-PS 7 418 913, DE-OS 28 02 989, DE-OS 28 37 687, DE-OS 25 23 991, EP-A 095 893, DE-OS 27 12 987 and DE-OS 27 16 004.

According to the invention, particularly preferred PEBA polymers are those which, in contrast to those described above, are built up on a random basis. To prepare these polymers, a mixture of
  1. one or more polyamide-forming compounds from the group of $\alpha,\omega$-aminocarboxylic acids and lactams with at least 10 carbon atoms,
  2. an $\alpha,\omega$-dihydroxy-polyoxyalkylene glycol,
  3. at least one organic dicarboxylic acid
in a ratio by weight of 1:(2+3) between 30:70 and 98:2, wherein equivalent amounts of hydroxyl groups and carbonyl groups are present in (2+3), is heated to temperatures of between 23° C. and 30° C. in the presence of 2 to 30 percent by weight of water, with respect to the polyamide-forming compounds in group 1, under the intrinsic pressure which becomes established, and then, after removing water, is further treated at 250 to 280° C. with the exclusion of oxygen, under atmospheric pressure or under reduced pressure.

The types of particularly suitable PEBA polymers are described, for example, in DE-OS 27 12 987.

Suitable PEBA polymers are obtainable, for example, under the commercial names PEBAX® from Atochem, Vestamid® from Hüils AG, Grilamid® from EMS-Chemie and Kellaflex® from DSM.

The PEBA polymers described are characterised by a very good set of physical properties. The Shore hardness can be varied over a wide range (Shore 70 A–Shore 60 D), depending on the composition of the PEBA polymer. The more plastic formulated PEBA formulations, as compared with comparable thermoplastic polyurethanes (TPUs), are characterised by exceptional processability. Due to the use of more plastic polymer materials, the risk of injuring vascular walls is greatly reduced. In addition, the moduli of the PEBA polymers are higher than those of thermoplastic polyurethanes with the same hardness.

On the basis of these specific properties, PEBA polymers are suitable for the production of medical devices, in particular catheters.

Furthermore, active substance-containing polyether block amides according to the invention may contain conventional plastics additives. Conventional additives are, for example, lubricants such as fatty acid esters, their metal soaps, fatty acid amides and silicon compounds, antiblocking agents, inhibitors, stabilisers against hydrolysis, light, heat and discoloration, fireproofing agents, colorants, pigments, inorganic or organic fillers and reinforcing agents. Reinforcing agents are in particular fibrous reinforcing substances such as inorganic fibres which are prepared according to the prior art and may also be provided with size. More detailed data relating to the auxiliary substances and additives mentioned may be found in the specialist literature, for example R. G ächter, H. Müller (eds): Taschenbuch der Kunststoff-Additive, 3rd edition, Hanser Verlag, Munich 1989, or DE-A 29 01 774.

Systematic investigations have shown that homogeneous distribution of the antimicrobial active substance in the polymer matrix is required in order to be able to use diffusion of the active substance as an adjustable release mechanism. The antimicrobial active substance and the polymeric supporting material used should therefore have a high physico-chemical compatibility. One measure of the compatibility of active substance and matrix is the interfacial energy occurring in the system. If this is high, then active substance and matrix are not very compatible and the active substance is released rapidly. If the interfacial energy is too low, the active substance is strongly bonded by the polymer matrix; release of effective amounts at the surface does not take place. In the case of good physico-chemical compatibility of active substance and matrix, a high coefficient of diffusion for the active substance in the polymer is produced. The actual rate of release of antimicrobial active substance in this case can be regulated by varying the amount of active substance incorporated since then the amount of active substance released is proportional to the concentration in the matrix.

To prepare active substance-containing polyether block amides according to the invention, combinations of matrix and active substance which have an interfacial energy of 0.5 to 30 mN/m, in particular 5 to 15 mN/m, are preferably selected.

Active substance-containing polyether block amides according to the invention are characterised in that they have a molecular disperse distribution of antimicrobial active substance in the polymer matrix. The high morphological homogeneity of the extruded active substance-containing plastics material can be shown using visible light and scanning electron microscope images. In addition, it can be demonstrated with the assistance of scanning electron microscope images that the polymer has a smooth surface before and after release of the incorporated active substance, i.e. biocompatibility of the polymer surface is not impaired either by the addition or by the release of the active substance.

Also, the mechanical properties of the polymer are not impaired by adding antimicrobial active substances in amounts of 0.1 to 10 wt. %. An improvement in mechanical properties has even been observed for specific material/active substance combinations.

Comparable active substance-containing samples which have been prepared using the cast film method (solvent casting), however, are much more inhomogeneous. Scanning electron microscope studies show that the active substances incorporated in the polymer matrix and on the surface are sometimes present in the form of groups of crystals. The groups of crystal bring about a deterioration in the mechanical properties of the polymer. In addition, groups of crystals which have been leached out leave a rough surface, which leads to reduced biocompatibility.

Moulded articles according to the invention may be prepared by extruding a molten material consisting of polymer and active substance. The molten material may contain 0.01 to 10 wt. %, preferably 1 to 5 wt. %, of active substance. The components may be physically mixed using known techniques, in any way at all. The active substance may be incorporated, for example, in solid form directly into the polymer melt. Also, an active substance-containing masterbatch may be melted directly with the polymer or may be mixed with the already molten polymer. The active substance may also be applied to the polymer before melting the polymer, using known techniques (by tumbling, drizzling, etc.).

In general, mixing/homogenisation of the components may be performed by known techniques using compounding or screw machines, preferably in single- or twin-screw extruders in a temperature range between 150 and 200° C.

A homogeneous, molecular disperse distribution of active substance in the polymer matrix is achieved by mixing the components during the extrusion process without having to involve any additional working stages.

Shaping takes place by the known techniques of thermoplastic processing (injection moulding, parison take-off, etc.). The moulded items are speck-free, flexible and non-tacky and may be sterilised without any problem using conventional processes.

EXAMPLES

Example 1 (Comparison)

Commercially available polyether block amide PEBAX® (Elf-Atochem Co., Philadelphia, Pa. 19103-3222).

Example 2

10 g of active substance were applied to 990 g of active substance-free PEBAX® in an intensive mixer. The active substance-containing cylindrical granules were extruded in a ZSK1 twin-shaft extruder. A clear molten material was obtained which produced colourless, clear cylindrical granules after cooling in a water/air bath and strand pelletisation.

The granules were each injection moulded to form test pieces (sheets) for microbiological in vitro tests and for determining the release profile of the incorporated active substance.

| Example | Active substance incorporated |
|---------|-------------------------------|
| 2a | kanamycin disulfate |
| 2b | gentamicin sulfate |
| 2c | ciprofloxacin betaine |
| 2d | doxycyclin HCl |
| 2e | clindamycin HCl |
| 2f | lincomycin HCl |
| 2g | fusidic acid |
| 2h | bacitracin |

Example 3

50 g of kanamycin disulfate were applied to 950 g of active substance-free PEBAX® in an intensive mixer. The active substance-containing cylindrical granules were extruded in a ZSK1 twin-shaft extruder. A clear molten material was obtained which produced colourless, clear cylindrical granules after cooling in a water/air bath and strand pelletisation.

Example 4

To prepare an active substance-containing masterbatch, 380 g of active substance-free cylindrical granules of the polyether block amide PEBAX® were dissolved in a suitable solvent (e.g chloroform) and 20 g of kanamycin disulfate were added thereto. The mixture was heated (about 70° C.) until a colourless homogeneous solution was obtained. After removing the solvent at 65° C./15 mbar, colourless, slightly opaque polymer sheets were obtained which were then granulated using a chopping machine.

400 g of the 5 wt. % strength masterbatch were mixed with 1600 g of active substance-free cylindrical granules and extruded on a ZSK1 twin-shaft extruder. A clear molten material was obtained which produced colourless, clear cylindrical granules after cooling in a water/air bath and strand pelletisation.

Example 5

To prepare an active substance-containing masterbatch, 380 g of active substance-free cylindrical granules of the polyether block amide PEBAX® were dissolved in a suitable solvent (e.g. chloroform) and 20 g of gentamicin sulfate were added thereto. The mixture was heated (about 70° C.) until a colourless, homogeneous solution was obtained. After removing the solvent at 65° C./15 mbar, colourless, slightly opaque polymer sheets were obtained which were then granulated using a chopping machine.

400 g of the 5 wt. % strength masterbatch were mixed with 1600 g of active substance-free cylindrical granules and extruded on a ZSK1 twin-shaft extruder. A clear molten material was obtained which produced colourless, clear cylindrical granules after cooling in a water/air bath and strand pelletisation.

Example 6

To prepare an active substance-containing masterbatch, 380 g of active substance-free cylindrical granules of the polyether block amide PEBAX® were dissolved in a suitable solvent (e.g. chloroform) and 20 g of bacitracin were added thereto. The mixture was heated (about 70° C.) until a colourless, homogeneous solution was obtained. After removing the solvent at 65° C./15 mbar, colourless, slightly opaque polymer sheets were obtained which were then granulated using a chopping machine.

400 g of the 5 wt. % strength masterbatch were mixed with 1600 g of active substance-free cylindrical granules and extruded on a ZSK1 twin-shaft extruder. A clear molten material was obtained which produced colourless, clear cylindrical granules after cooling in a water/air bath and strand pelletisation.

Example 7

S2 tensile bars were punched out from the specimen sheets of materials prepared in examples 1, 2a, 2b and 2h and the strength characteristics in accordance with DIN 53 455 were determined. The tension sets of the specimens were determined in a similar way to that described in DIN 53 518. Determination of the E-moduli was performed in accordance with DIN 53 457.

The results of the tests are summarised in table 1. They show that the thermal/mechanical properties of unfilled PEBAX® are not significantly altered by adding antimicrobial active substances, within the context of the accuracy of measurement.

TABLE 1

Thermal/mechanical properties of unfilled PEBAX® and of active substance-containing PEBAX® samples.

| Measured value | Example 1 PEBAX® | Example 2a PEBAX® + 1 wt. % of kanamycin | Example 2b PEBAX® + 1 wt. % of gentamicin | Example 2h PEBAX® + 1 wt. % of bacitracin |
|---|---|---|---|---|
| Tensile strength [MPa] | 22.0 | 20.3 | 21.0 | 22.3 |
| Elongation at break [%] | 1080 | 995 | 1058 | 1073 |
| Residual elongation at 200% elongation | 46 | 49 | 45 | 46 |
| E' (10° C.) [MPa] | 79 | 107 | 114 | 89 |
| E' (36° C.) [MPa] | 24 | 35 | 40 | 27 |

Example 8

Determination of the release profiles of active substance-containing polymer samples was performed by elution in Millipore water (0.1% $NaN_3$). In a typical experiment, 20 ml of Millipore water were added to 5 g of active substance-containing polymer platelets made of PEBAX® (area: 1 $cm^2$) at 37° C. and stirred at a constant speed. The elution agent was removed at regular time intervals of 24 h, for quantitative determination of the active substance content, and replaced by fresh Millipore water. Quantification of the active substance released in the corresponding solutions was performed using HPLC analysis. All experimental series were performed twice, quantitative determination of the active substance content was performed each time as a double determination.

The results of the tests are summarised in table 2. They show that the active substance-containing polymers continuously release the corresponding antimicrobial active substance at the surface over a long period of time (2 weeks). In addition, it can be shown that active substance diffusion out of the polymer can be used as an adjustable release mechanism: the higher the amount of active substance incorporated, the greater is the concentration of active substance released from the polymer matrix into the elution medium.

TABLE 2

Release profiles of active substance-containing polymer samples. The concentration [mg/l] of active substance released from the polymer samples is cited each time. Example 1: control sample, active substance-free PEBAX ®, Example 2c: 1.0 wt. % ciprofloxacin betaine in PEBAX ®, Example 2d: 1.0 wt. % doxycyclin HCl in PEBAX ®, Example 2e: 1.0 wt. % clindamycin HCl in PEBAX ®, Example 2f: 1.0 wt. % lincomycin HCl in PEBAX ®, Example 2g: 1.0 wt. % fusidic acid in PEBAX ®

| Time [h]   | 0 | 22     | 45    | 69    | 93    | 165   | 189    | 213    | 237    | 261    |
|------------|---|--------|-------|-------|-------|-------|--------|--------|--------|--------|
| Example 1  | 0 | 0      | 0     | 0     | 0     | 0     | 0      | 0      | 0      | 0      |
| Example 2c | 0 | 88.13  | 135.2 | 183.5 | 230.5 | 279.1 | 321.0  | 353.7  | 387.0  | 417.5  |
| Example 2d | 0 | 537.77 | 730.2 | 834.8 | 898.4 | 995.1 | 1032.4 | 1052.9 | 1069.5 | 1085.2 |
| Example 2e | 0 | 331.61 | 453.0 | 540.2 | 603.8 | 702.7 | 746.2  | 781.7  | 816.0  | 847.1  |
| Example 2f | 0 | 286.01 | 371.4 | 427.3 | 463.8 | 540.1 | 566.   | 588.4  | 610.5  | 630.5  |
| Example 2g | 0 | 15.1   | 20.4  | 27.0  | 34.5  | 42.5  | 52.0   | 61.6   | 70.8   | 80.5   |

Example 9

Testing the antimicrobial efficacy of modified polymers was performed with the bacteria strains *S. epidermidis* 0–47– and *S. epidermidis* 0–47+ (bioMerieux Co., D-72622 Nürtingen) and also the test strains *S. aureus* ATCC 25923, *S. epidermidis* ATCC 14990 and *S. saproph.* ATCC 43867.

The bacteria strains were each cultivated in an overnight culture on standard II nutrient agar (Merck KGaA, D-64293 Darmstadt) and suspended in NaCl solution (0.85%). The bacteria suspensions obtained, with a density of 0.5 MacFarland, were diluted 1:100 in NaCl solution (0.85%) and applied to agar plates (Mueller-Hinton Agar, Merck KGaA, D-64293 Darmstadt). The 1 cm² polymer samples were sterilised, placed under slight pressure on the agar plates and incubated at 37° C. for 20 hours. After incubation, the agar plates were checked for inhibition halos and the extents of the inhibition halos were measured.

test series (3 different polymer samples and 7 test strains) were performed. The results of the agar diffusion tests are summarised in table 3. They show that an inhibition zone was produced around the active substance-containing polymer samples, as compared with the active substance-free samples, in which no bacterial growth occurred, i.e. the active substance-containing polymer samples exhibited a substantial antimicrobial effect towards the test strains used.

What is claimed is:

1. A thermoplastic molding composition comprising:
   (a) a polyether block amide polymer having repeat units represented by the following formula (I),

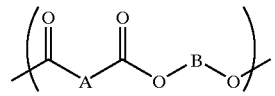

wherein
   A is a residue of a polyamide having 2 terminal carboxylic acid groups, and
   B is a residue of a polyoxyalkylene glycol having terminal OH groups; and
   (b) at least one homogeneously distributed antimicrobially active substance selected from at least one of (i) nalidixic acid, pipemidics acid, cinoxacin, ciprofloxacin, norfloxacin, ofloxacin, perfloxacin and enoxacin; (ii) aminoglycosides; (iii) macrolides; (iv) polypeptides; (v) lincomycins; (vi) antimycobacterial agents; and (vii) fusidic acid,
   provided that said polyether block amide (a) and said antimicrobially active substance (b) have an interfacial energy of 0.5 to 30 mN/m.

2. A molded article comprising the composition of claim 1.

3. The composition of claim 1 wherein said active substance (b) is present in an amount such that a molded article

TABLE 3

Testing the antimicrobial efficacy of active substance-free and active substance-containing polymer samples towards different test strains in an agar diffusion test. The antimicrobial effect is indicated by the production of an inhibition halo. The diameter of the inhibition halos are given in mm.

|                                           | S. epid. 0-47–* | S. epid. 0-47+* | S. aureus 851 | S. epid. 653 | S. aureus ATCC 25923 | S. epid. ATCC 14990 | S. saproph ATCC 43867 |
|-------------------------------------------|-----------------|-----------------|---------------|--------------|----------------------|---------------------|-----------------------|
| Example 1 PEBAX ® (control)               | 0               | 0               | 0             | 0            | 0                    | 0                   | 0                     |
| Example 2a PEBAX ® + 1 wt. % of kanamycin | >19             | >19             | 0             | 0            | >19                  | >19                 | >19                   |
| Example 2b PEBAX ® + 1 wt. % of gentamicin| >19             | >19             | >19           | 0            | >19                  | >19                 | >19                   |

*source: bioMerieux Co., D-72622 Nürtingen prepared from said composition is free of surface colonization by bacteria for a period of 2 to 4 weeks.

4. The composition of claim 1 wherein said active substance (b) is present in an amount of 0.01 to 10 percent by weight, based on the weight of said composition.

5. The composition of claim 1 wherein said active substance (b) is selected from at least one of nalidixic acid, pipemidic acid, cinoxacin, ciprofloxacin, norfloxacin, ofloxacin, perfloxacin and enoxacin.

6. The composition of claim 5 wherein said active substance (b) is ciprofloxacin.

7. The composition of claim 1 wherein said polyether block amide (a) and said antimicrobially active substance (b) have an interfacial energy of 5 to 15 mN/m.

8. The composition of claim 1 wherein the amount of said polyoxyalkylene glycol used in the preparation of said polyether block amide polymer (a) is from 5 to 85 percent by weight, based on the weight of said polyoxyalkylene glycol and said polyamide having 2 terminal coarboxylic acid groups.

9. The composition of claim 1 wherein the amount of said polyoxyalkylene glycol used in the preparation of said polyether block amide polymer (a) is from 10 to 50 percent by weight, based on the weight of said polyoxyalkylene glycol and said polyamide having 2 terminal coarboxylic acid groups.

10. The molded article of claim 2 wherein said molded article is a catheter.

11. A method of preparing a molded article comprising extruding the composition of claim 1.

* * * * *